United States Patent [19]
Nabahi

[11] Patent Number: 5,788,980
[45] Date of Patent: Aug. 4, 1998

[54] INTRAVAGINAL DRUG DELIVERY DEVICE

[75] Inventor: Shohre Nabahi, Swindon, England

[73] Assignee: Roussel Uclaf, France

[21] Appl. No.: 740,095

[22] Filed: Oct. 24, 1996

[30] Foreign Application Priority Data

Nov. 1, 1995 [GB] United Kingdom ............ 9522403

[51] Int. Cl.$^6$ ............................................. A61F 6/06
[52] U.S. Cl. .................... 424/430; 424/432; 424/433; 424/486
[58] Field of Search ...................... 424/430, 432, 424/433, 486

[56] References Cited

U.S. PATENT DOCUMENTS

| | | |
|---|---|---|
| 3,545,439 | 12/1970 | Duncan ........................ 128/260 |
| 4,155,991 | 5/1979 | Schopflin ........................ 424/15 |
| 4,286,587 | 9/1981 | Wong ........................ 128/127 |
| 4,292,965 | 10/1981 | Nash ........................ 424/22 |
| 4,308,867 | 1/1982 | Roseman ........................ 128/260 |
| 4,659,696 | 4/1987 | Hirai ........................ 514/15 |
| 4,822,616 | 4/1989 | Zimmerman ........................ 424/432 |

*Primary Examiner*—D. Gabrielle Brouillette
*Attorney, Agent, or Firm*—Bierman, Muserlian and Lucas

[57] ABSTRACT

An intravaginal drug delivery device for prolonged release of an active ingredient comprising a biocompatible polymer matrix containing an active ingredient to be released and an effective amount of at least one fatty acid ester and a method of inducing contraception in female warm-blooded animals, including humans.

19 Claims, 7 Drawing Sheets

INTRAVAGINAL DRUG DELIVERY DEVICE

17β-estradiol (E2) is the principal estrogen produced by the functioning pre-menopausal ovary during each menstrual cycle. With the ageing process, ovulation becomes less frequent, resulting in diminished production of E2. During menopause, E2 production decreases dramatically to less than 20 µg per day. Estrogen deficiency can also occur in the premenopausal female as a result of disease, traumatic injury or oophorectomy.

Estrogens, particularly 17β-estradiol, are widely used for treating estrogen deficiency, the aim being to replace endogenous estrogens lost due to ovarian failure. Of the naturally occurring estrogens, 17β-estradiol (E2) has the best therapeutic profile for Estrogen Replacement Therapy (ERT) and Hormone Replacement Therapy (HRT) and has been found to have an especially low incidence of side effects. In particular, 17β-estradiol does not stimulate clotting factor synthesis and is not associated with an increased risk of venous thrombosis. 17β-estradiol and its semi-synthetic esters are therefore widely used in the treatment of disorders associated with estrogen deficiency, particularly menopausal and post-menopausal symptoms.

When taken orally, estrogens are not particularly well absorbed, although reasonable systemic levels can be achieved after micronization. Oral administration is followed primarily by absorption through the gastrointestinal tract from where the blood flow is to the liver. In general, estrogens have a high first pass and about 70% is metabolized during the first pass through the liver. As a result, oral estrogen therapy results in the formation of estrone, a less potent estrogen, which influences the blood lipid profile. This also means that there is about a 30% reduction in availability of estrogen due to the first pass effect.

A further disadvantage associated with the oral administration of estrogen is that it involves bolus doses resulting in undesirably high estrogen levels after each dose and the need for frequent dosing.

Alternatives to oral administration include transdermal drug delivery systems and subcutaneous implantation of estrogen-containing pellets. Transdermal drug delivery systems are not capable of producing the levels of estrogen required for long term therapy and must be replaced every few days. Subcutaneous implants require surgical insertion and removal and are difficult to remove if dangerous side effects develop. Moreover, neither of these methods is capable of producing the constant levels of estrogen necessary for the treatment of estrogen deficiency over a long period of time.

Vaginal administration of estrogen overcomes a number of the problems associated with oral delivery. It is well known that steroids in general, including estrogens, are efficiently and rapidly absorbed through the vaginal mucosa. Moreover, delivery of estrogen into the vagina is analogous to the secretion of estrogen into the blood stream by the ovary and avoids undesirable first pass metabolism by the liver.

OBJECTS OF THE INVENTION

It is an object of the invention to provide a novel intravaginal drug delivery device for substantially constant release of an active ingredient over a prolonged period of time.

It is another object of the invention to provide a novel method of treating estrogen deficiencies in female warm-blooded animals over a period of time.

These and other objects and advantages of the invention will become obvious from the following detailed description.

THE INVENTION

The intravaginal drug delivery device of the invention for prolonged release of an active ingredient comprises a biocompatible polymer matrix containing an active ingredient to be released and an effective amount of at least one fatty acid ester.

Estrogen may be administered intravaginally using creams, solutions or tablets. However, as with oral administration, these result in bolus delivery rather than sustained levels of estrogen and require repeated application. To achieve controlled, sustained release of estrogen over a period of months, an intravaginal device, conveniently in the shape of a ring, has proved to be most effective. A particular advantage associated with the use of vaginal rings is that these can be self-inserted into and removed from the vagina.

There are three main types of ring design. The first is the matrix ring, also known as the homogeneous ring, in which the active ingredient is homogeneously distributed in a hydrophobic elastomeric system. In this design, high initial loading is possible, resulting in an initial high dose followed by a gradual decrease in the drug release rate. The rate of release is expressed by the equation given below (Chien 1985):

$$Q/t^{\frac{1}{2}} = (2 \, A \, Cp.Dp)^{\frac{1}{2}}$$

wherein

Q=amount of active ingredient released per unit area
A=concentration of the active ingredient in the matrix
Cp=solubility of active ingredient in the silicon matrix
Dp=diffusion coefficient of the active ingredient in the silicone matrix
t=time The rate of release of active ingredient expressed by this equation is not zero order. This design of ring is therefore unable to sustain a constant delivery of active ingredient over a prolonged period of time.

The second type of ring design is the core design in which the active ingredient is homogeneously dispersed in an elastomer core surrounded by a rate-controlling membrane. The rate of drug release from a ring of this type can be expressed by the following equation (Crank 1967):

$$R = \frac{2\pi Cs.D.L}{\ln(b/a)}$$

wherein

R=release rate
π=3.14
Cs=saturation solubility of active ingredient in the polymer matrix
D=diffusion coefficient of active ingredient in the polymer matrix
b=diameter of the sheath
a=diameter of the core
L=length of the core Delivery of doses in the range of from 50 to 100 µg per day of E2 from a ring of this type requires a core of large diameter used in combination with a particularly thin membrane. Membranes of the order of 0.5 to 1 mm required to achieve such a dose are highly susceptible to tearing during manufacture and during use and are also difficult to manufacture using current manufacturing methods.

The third type of ring is the shell design in which the drug is contained in a narrow band between a non-medicated central hydrophobic elastomeric core and a narrow outer non-medicated hydrophobic elastomeric sheath, wherein the outer sheath acts as a rate-controlling membrane. This design of ring is difficult to manufacture and is unable to deliver the therapeutic doses of estrogen required in hormone replacement therapy.

Stumpf et al. [Journal of Clinical Endocrinology and Metabolism 54(1): 208–210 (1982)] describes polysiloxane vaginal rings for the delivery of 17β-estradiol. Standard rings of a shell design having a central layer containing the estradiol were found to be ineffective in providing therapeutic delivery of 17β-estradiol over any significant period of time. Rings of homogeneous design were also studied which contained 400 mg of 17β-estradiol distributed homogeneously throughout a ring having a surface area of 22 cm$^2$ and a cross-sectional area of 48 mm$^2$. Although Stumpf suggests that such rings are capable of generating circulating levels of 17β-estradiol in the physiological range for at least 3 months, the levels of E2 reported are in fact unacceptably high for use in hormone replacement therapy. Moreover, these rings are characterized by a particularly high initial burst of steroid release during the first month of use followed by a gradual decline in release rate.

There thus exists a need for improved vaginal drug delivery devices capable of releasing estrogens, in particular 17β-estradiol, in a substantially zero order pattern on a daily basis over a period of several months.

Women who have undergone a hysterectomy with or without oophorectomy are at no risk from endometrial proliferation and can receive unopposed 17β-estradiol. However, for women with an intact uterus, 17β-estradiol therapy may conveniently be combined with a progestogen to reduce the risk of endometrial carcinoma.

It has now surprisingly been found that incorporation of a fatty acid ester into an intravaginal drug delivery device is able to produce the desired release rates of estrogen and/or progestogen over several months.

Thus, viewed from one aspect, the invention provides an intravaginal drug delivery device containing an estrogen and/or a progestogen in a polymer matrix, wherein the polymer matrix further contains at least one fatty acid ester, preferably of 2 to 20 carbon atoms. Preferably, the polymer matrix is surrounded by a rate-controlling membrane.

Although not wishing to be bound by theoretical considerations, it is believed that the fatty acid ester serves to increase the hydrophilicity of the polymer matrix, thus increasing the solubility of the estrogen in the matrix and hence increasing the rate of release of estrogen from the device. This enables delivery of sustained, therapeutic quantities of estrogen over extended periods of time, such as required in Estrogen Replacement Therapy (ERT) and Hormone Replacement Therapy (HRT).

Preferred fatty acid esters for use in the device of the invention include those formed from fatty acids of 2 to 20 carbon atoms, especially long chain fatty acids such as caproic acid, lauric acid, myristic acid, oleic acid, linoleic acid, adipic acid, and lanolic acid. Particularly preferred are those esters formed from myristic acid.

Alcohols which may be used in the formation of the esters include those of 2 to 20 carbon atoms, preferably alkanols of 2 to 4 carbon atoms, e.g. propanol, more preferably isopropanol. A particularly preferred fatty acid ester is isopropyl myristate.

The polymer matrix may comprise one or more biocompatible polymers such as elastomers like organopolysiloxanes. Preferred elastomers include hydroxyl-terminated organopolysiloxanes of the RTV (room temperature vulcanizing) type which harden to elastomers at room temperature following the addition of cross-linking agents in the presence of curing catalysts.

Suitable cross-linking agents and curing catalysts are known in the art. A typical curing catalyst is stannous octoate. Curing temperature and curing times can vary within broad ranges and depend on the particular elastomer used. The curing temperature may vary between room temperature and 150° C., but is preferably within 60° to 90° C. The curing time may vary between a few seconds to several hours.

Other suitable elastomers include two-component dimethylpolysiloxane compositions which are platinum catalyzed at room temperature or at elevated temperatures and capable of addition cross-linking.

Preferred hydrophobic elastomers for use in the device of the invention include Silastic 382® and Silastic 4210®, both commercially available from Dow Corning.

The rate-controlling membrane may comprise any biocompatible polymer. Conveniently, this will comprise the same polymer as the polymer matrix.

The polymer matrix and/or the rate-controlling membrane may further comprise one or more filler materials such as diatomaceous earth or silica. In addition, the polymer matrix may contain an X-ray contrast medium such as barium sulfate, which can be used for identification purposes.

While it should be apparent that the intravaginal device of the invention may have any shape and dimension compatible with intravaginal administration, a preferred device of the invention is in the form of a ring which conveniently comprises a central polymer matrix core surrounded by the rate-controlling membrane.

Conveniently, the overall diameter of the ring is in the range of 52 to 62 mm, with a sheath diameter (cross-sectional diameter of the ring) in the range of 4 to 10 mm and a core diameter in the range of 1 to 9 mm. The diameter of the rate-controlling membrane is such that it can be manufactured within acceptable tolerances by methods known in the art and conveniently lies within the range of from 1 to 4 mm, preferably 2 to 3 mm. The geometry of the ring may be selected depending on the required daily dose of estrogen and the duration of the course of treatment.

It will be appreciated that the desired amount of estrogen present in the device will depend on the particular estrogen being administered as well as the condition being treated. Convenient amounts of estrogen present in the device are 1 to 50% by weight, preferably up to 15% by weight, more preferably from 5 to 15% by weight.

The amount of fatty acid ester present in the device will also clearly depend upon the particular estrogen to be delivered as well as the condition to be treated. Conveniently, the amount of fatty acid ester present in the device is 1 to 50% by weight, preferably from 5 to 20% by weight. It has been found that by adjusting the level of fatty acid ester present in the polymer matrix, a range of doses of estrogen from rings of similar geometry can be achieved.

The device of the invention can be used to effectively treat a number of conditions resulting from estrogen deficiency, e.g. vasomotor symptoms associated with estrogen deficiency, atrophic vaginitis, atrophic urethritis and osteoporosis associated with estrogen deficiency. The device is particularly effective in hormone and estrogen replacement therapies. Since fertility control involves the administration of sufficient estrogen to prevent ovulation, it will be appreciated that the delivery device of the invention may also be used to prevent ovulation and thus act as an effective contraceptive.

Estrogens which can be delivered vaginally using the device of the invention include estrone and estriol, particularly 17β-estradiol which is widely used in hormone replacement therapy (HRT). Constant, daily release rates up to 500 μg per day for a period of up to 12 months can be achieved using a device of the invention. The desired rate of release of estrogen depends on the condition to be treated but can be varied over a range of from 10 to 200 μg per day. A physiologically effective dose of 17β-estradiol sufficient to treat postmenopausal symptoms is considered to be of the order of at least 50 μg per day.

Progestogens which can be delivered vaginally using the device of the invention include any progestogens known to be suitable for use in hormonal replacement therapy. Preferred progestogens include progesterone, medroxyprogesterone, norethisterone, trimegestone and norethisterone acetate. Convenient amounts of progestogen present in the device are 1 to 50% by weight, preferably up to 15% by weight, more preferably 5 to 15% by weight.

Progestogen and estrogen which can be delivered vaginally using the device of the invention include in particular trimegestone in association with 17β-estradiol.

Intravaginal drug delivery devices of the invention can be prepared by methods well known in the art, such as injection molding techniques or by extrusion of a polymer mixture. The geometry of the devices can be varied by the use of appropriately sized molds or appropriately sized extrusion dies.

Viewed from a further aspect, the invention provides a method for the manufacture of an intravaginal drug delivery device as hereinbefore defined, said method comprising the steps of combining estrogen and/or a progestogen together with a fatty acid ester in a polymer matrix to form a core; and optionally surrounding said core with a rate-controlling membrane.

In the following examples, there are described several preferred embodiments to illustrate the invention. However, it should be understood that the invention is not intended to be limited to the specific embodiments.

EXAMPLE 1

A silicone mix was prepared by mixing 97% by weight of polydimethylsiloxane (Silastic 3099 from Dow Corning) with 2.5% by weight of the cross-linking agent, n-propylorthosilicate. The resulting mix was then blended in a ratio of 80 to 95% by weight with from 5 to 20% by weight of isopropyl myristate (mix 1). 5% by weight of 17β-estradiol was then added and mixed thoroughly. Appropriate quantities of the above mix were then weighed and 0.5% by weight of the catalyst, stannous octoate, was added and the mixture was mixed for 1 minute. The final mix was then injected into 2 mm core molds and subsequently cured at 80° C. for 2 minutes.

The active cores were then removed from the molds and placed in a second mold and a sheath was formed around the core by two-stage injection molding of mix 1 together with 0.5% by weight of catalyst.

Figure 1:
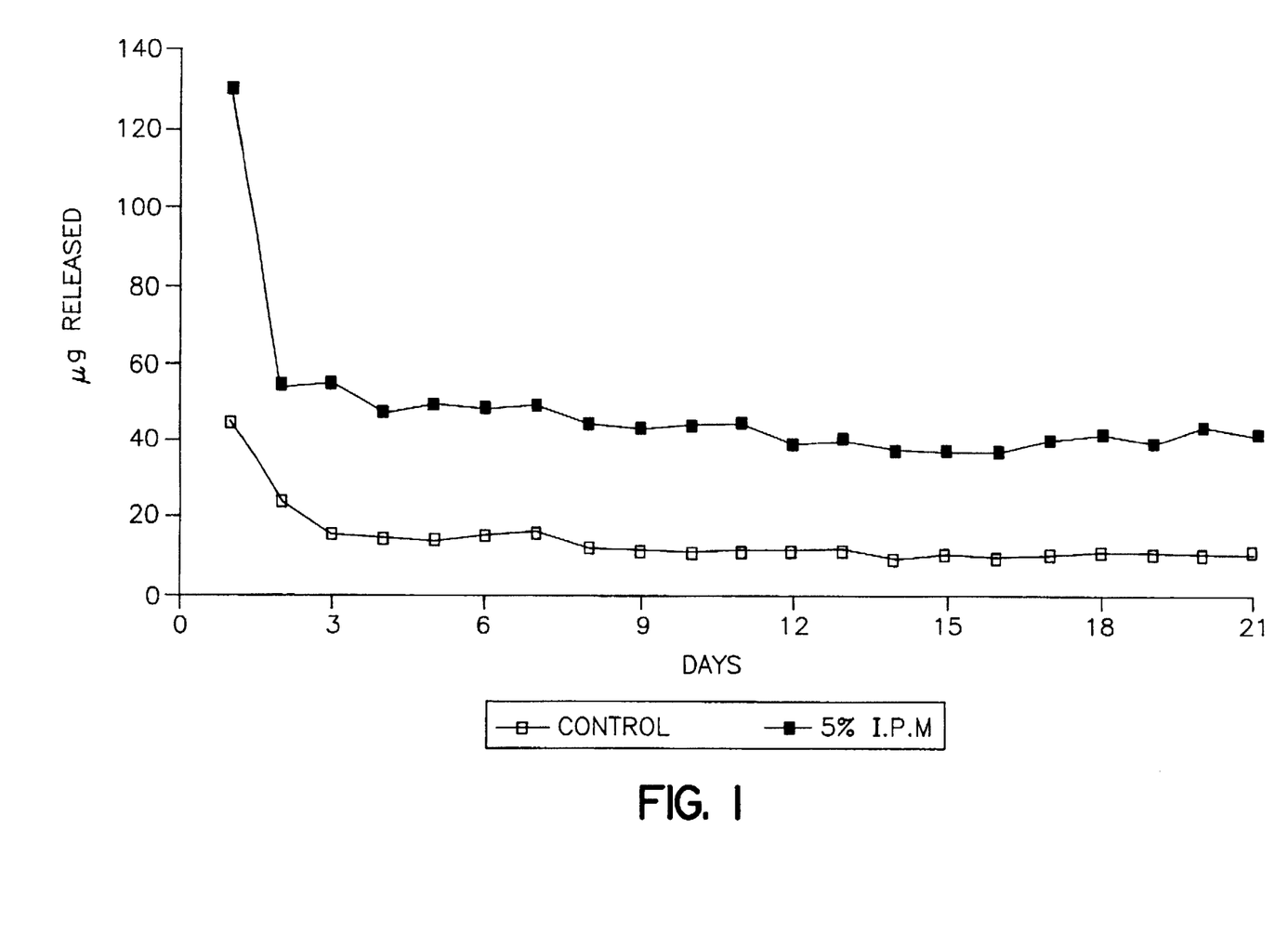
FIG. 1 is a graph showing the rate of release of estradiol from a ring with a core diameter of 2 mm, a sheath diameter of 7.6 mm and a membrane thickness of 2.8 mm.

The rings were subjected to in vitro release testing in 1 liter of water as release medium at 37° C. Release of 17β-estradiol from rings containing 5% by weight of isopropyl myristate over the 21 day period of the test is shown in FIG. 1. A zero release rate of 40 μg per day was achieved.

EXAMPLE 2

Figure 2:
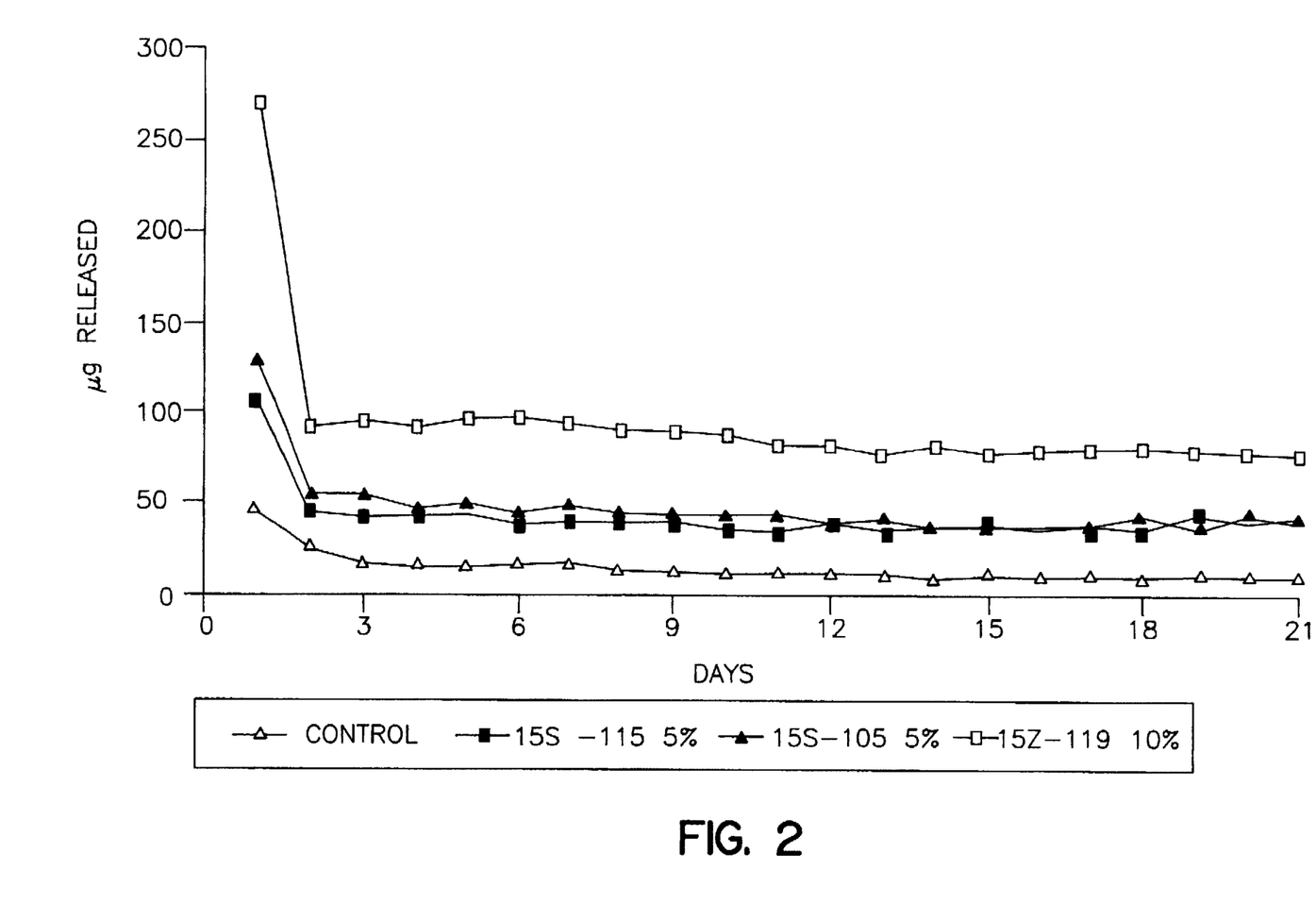
FIG. 2 is a graph showing the rate of release of estradiol with a ring of FIG. 1 with 10% by weight of isopropyl-myristate.

A second set of rings containing 10% by weight of isopropyl myristate were produced as in Example 1. The rings were subjected to in vitro release testing in 1 liter of water as release medium at 37° C. The rate of release of 17β-estradiol from these rings can be seen in FIG. 2. A zero order release rate of 80 μg per day was achieved.

EXAMPLE 3

Silastic 4210® (from Dow Corning) was blended in a ratio of 80 to 95% by weight with from 5 to 20% by weight of isopropyl myristate (mix 1). 5% by weight of 17β-estradiol was then added and the mixture was mixed thoroughly. 7 parts of the above mix were then weighed and 1 part of curing agent was added and the mixture was mixed for 1 minute. The final mix was then injected into 2 mm core molds and subsequently cured at 80° C. for 2 minutes.

The active cores were then removed from the molds and placed in a second mold and a sheath was then formed around the core by two-stage injection molding of 7 parts of mix 1 and 1 part of curing agent.

The rings were subjected to in vitro release testing in 1 liter of water as release medium at 37° C. A zero order release rate of 60 μg of 17β-estradiol per day was achieved from rings containing 10% by weight of isopropyl myristate.

EXAMPLE 4

Figure 3:
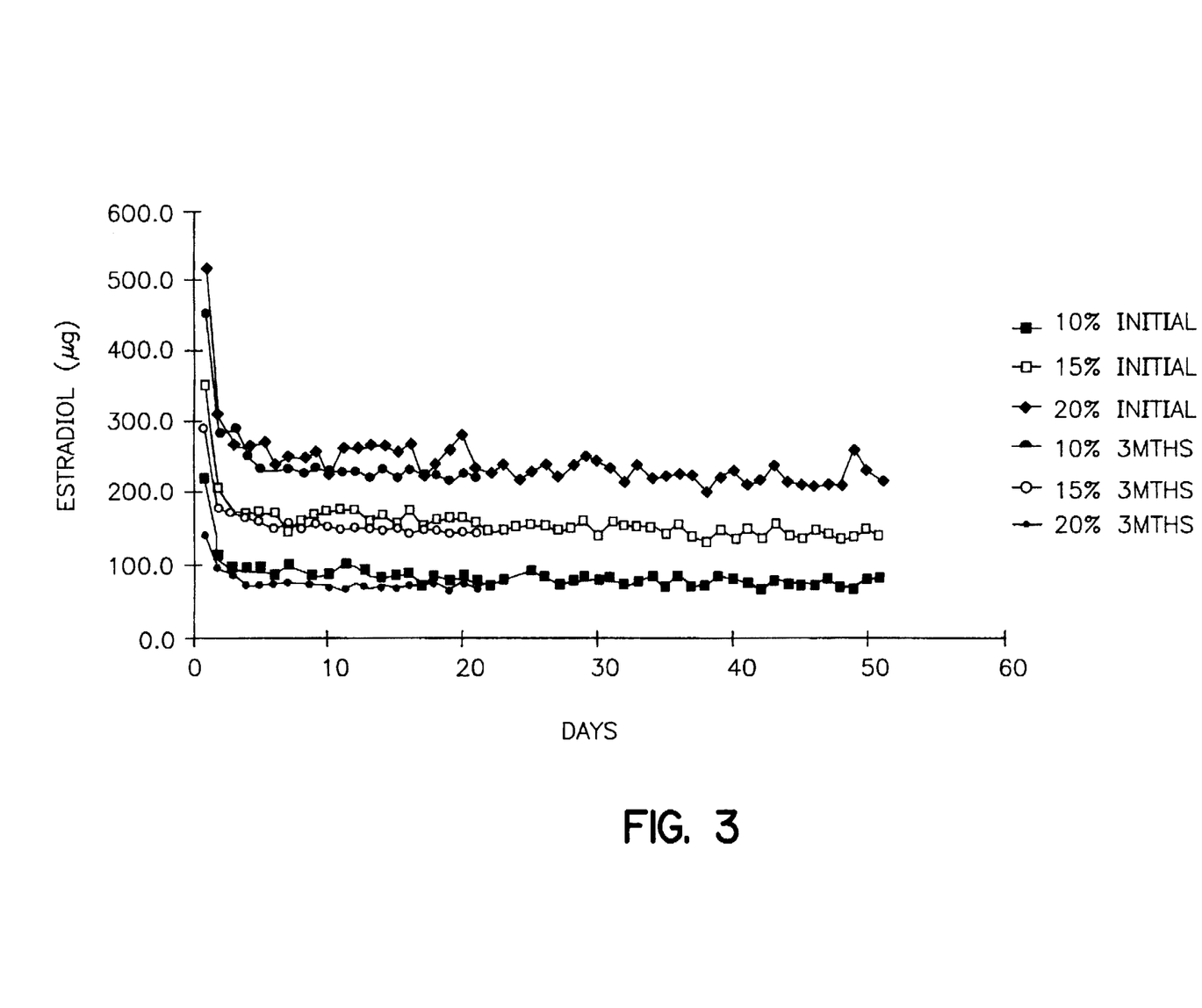
FIG. 3 is a graph showing the release rate of rings with 10, 15 and 20% by weight of isopropyl-myristate after three months of storage.

Rings were manufactured as per Example 1 using 10, 15 and 20% by weight of isopropyl myristate. The rings were release tested over 50 days. Zero order release rates of 80, 160 and 240 μg were obtained. After 3 months of storage at 25° C., the release was as per initial (FIG. 3).

EXAMPLE 5

Figure 4:
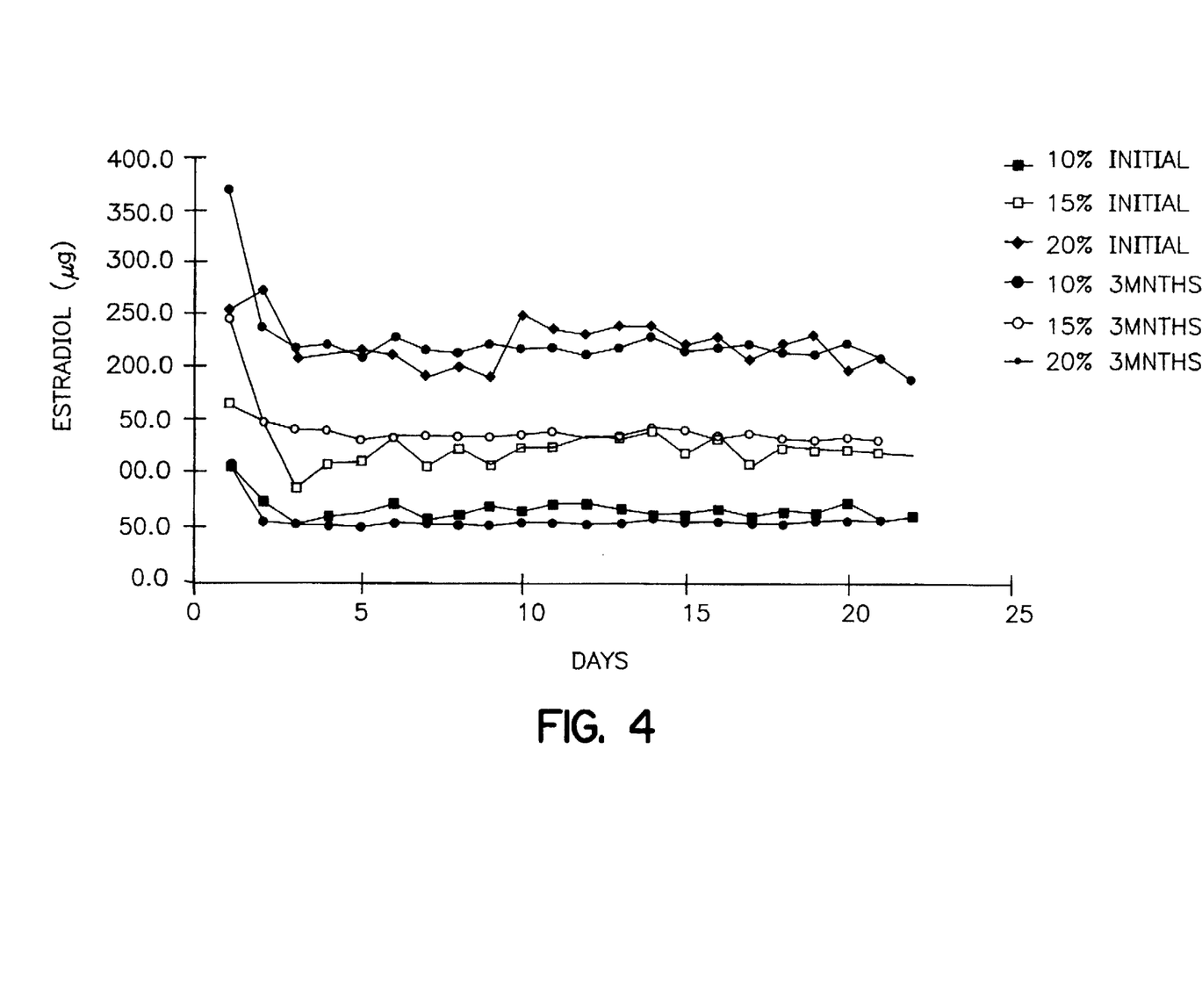
FIG. 4 is a graph showing the release rate of rings with 10, 15 and 20% by weight of Silastic 4210 after three months of storage.

Further batches of rings were also manufactured using Silastic 4210® exactly as per Example 3. FIG. 4 presents the results of the release testing (initial and after 3 months of storage at 25° C.).

EXAMPLE 6

Figure 5:
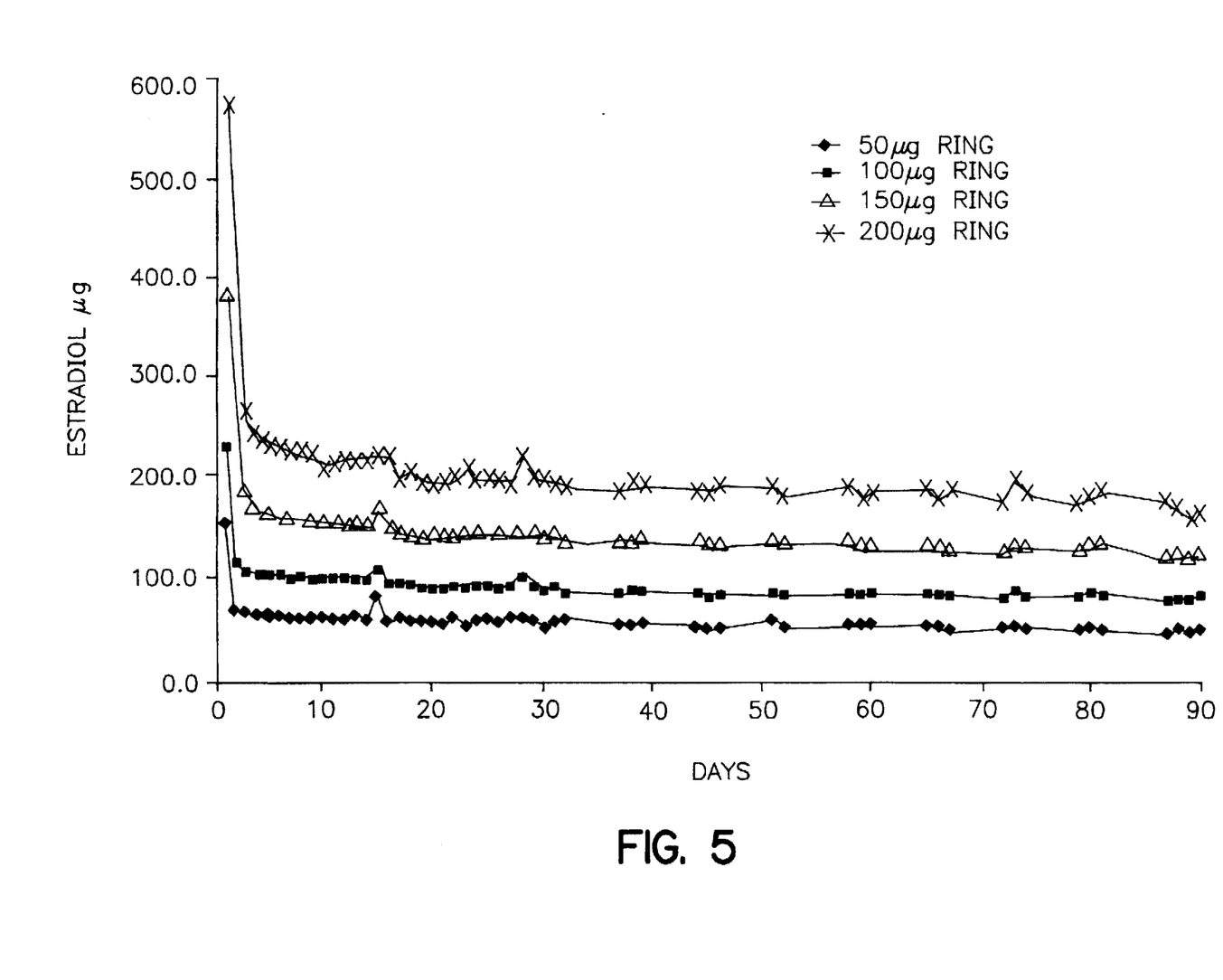
FIG. 5 is a graph showing the release rate with a ring with a core of 4.5 mm using 2.5 to 10% by weight of isopropyl-myristate.

Rings were manufactured as per Example 1 using 5% by weight of 17β-estradiol and 2.5 to 10% by weight of isopropyl myristate and a core size of 4.5 mm was used for these rings. The rings were release tested and zero order release rates were observed over 90 days (FIG. 5).

Although the invention has been described with particular reference to 17β-estradiol, it extends also to intravaginal drug delivery devices for the administration of other active ingredients. Such devices can be made by methods analogous to those described above but in which the 17β-estradiol is replaced by the active ingredient required.

EXAMPLE 7

A silicone mix was prepared as per Example 1 using 10% by weight of isopropyl myristate (mix 1). 5% by weight of mifepristone was then added to a portion of the above and cores were manufactured using 4.5 mm moulds. A sheath was then formed around the core by two stage injection mouldings of mix 1 as per Example 1.

Figure 6:
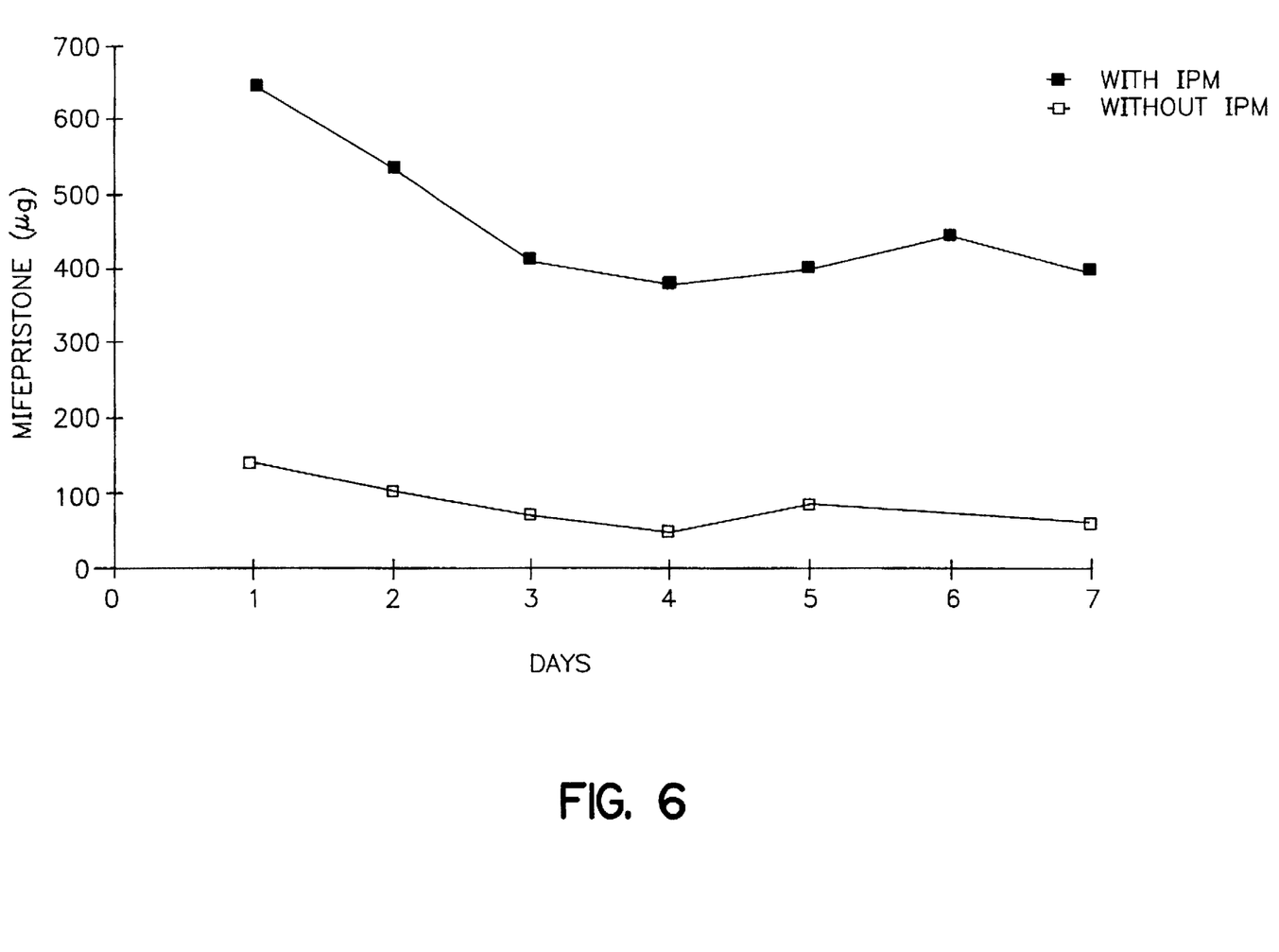
FIG. 6 is a graph of release rates of mifepristone with and without the presence of isopropyl-myristate.

The above procedure was repeated without the use of isopropyl myristate in the silicone mix. The rings were subjected to in vitro release testing in 1 liter of water as release medium at 37° C. Zero order release rates of 400 μg per day and 100 μg per day was recorded respectively. The addition of isopropyl myristate results in a four fold increase in the release rate of the active while maintaining the zero order profile (FIG. 6).

EXAMPLE 8

Figure 7:
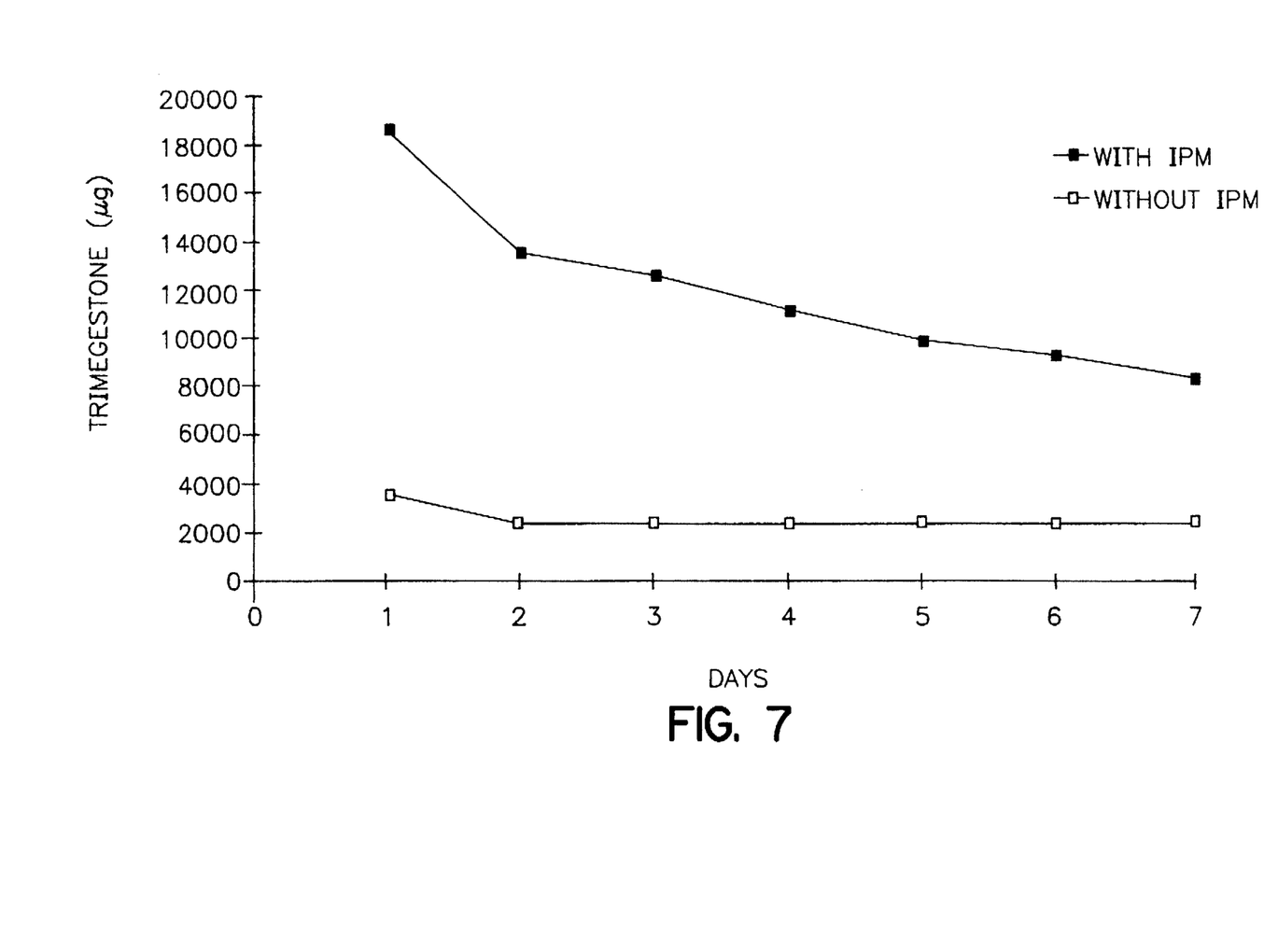
FIG. 7 is a graph of release rates of trimegestone with and without the presence of isopropyl-myristate.

A second set of rings were prepared exactly as per Example 7 using Trimegestone as the active substance in the core. The rings were release tested. The addition of isopropyl myristate increased the release rate by five fold while maintaining the zero order profile (FIG. 7).

CONCLUSION

The above examples show that the fatty acid esters serves to increase the hydrophilicity of the polymer matrix, thus increasing the solubility of the active substance in the matrix and hence increasing the rate of release of the active from the device. This enables delivery of sustained, therapeutic quantities of a number of active molecules over extended periods of time.

Thus, viewed from a broader aspect, the invention provides an intravaginal drug delivery device comprising an active ingredient in a polymer matrix, wherein the polymer matrix further comprises at least one fatty acid ester, preferably containing from 2 to 20 carbon atoms.

Suitable alternative active ingredients and their therapeutic use are listed by way of example only in the following table:

| ACTIVE COMPOUND | CATEGORY |
| --- | --- |
| Fluphenazine | Antidepressants/Anxiolitics |
| Flupenthixol | |
| Haloperidol | |
| Buspirone | P.M.S. Anxiolitics |
| Alprazolam | |
| Trifluoperazine | |
| Pyridoxine | P.M.S. Vitamin B6 |
| Pyridoxal | |
| Pyridoxamine | |
| Cholecalciferol | Vitamin D |
| Dihydrotachysterol | |
| Ergocalciferol | |
| Alfacalcidol | |
| d-Alpha Tocopherol | Vitamin E |
| Clotrimazole | Antifungal |
| Enconazole | |
| Itraconazole | |
| Buprenorfine | Opiod Analgesics |
| Levorphanol | |
| Phenoperidine | |

-continued

| ACTIVE COMPOUND | CATEGORY |
| --- | --- |
| Fentanyl | |
| Methadone | |
| Metanamic Acid | Non-Opiod Analgesics |
| Acyclovir | Antiviral |
| Vidarabine | |
| Arildone | |
| Idoxuridine | |
| Cestrinone | Endometriosis |
| Mifepristone | |

Various modifications of the drug delivery device and method of preventing contraception may be made without departing from the spirit or scope thereof and it is to be understood that the invention is intended to be limited only as defined in the appended claims.

What is claimed is:

1. An intravaginal drug delivery device for prolonged release of an active ingredient consisting essentially of at least one polyorganosiloxane ring matrix containing an active ingredient to be released, and an amount of 1 to 50% by weight of at least one fatty acid ester.

2. A device of claim 1 wherein said fatty acid ester is present in an amount of from 5 to 20% by weight.

3. A device of claim 1 wherein said fatty acid ester is formed from a fatty acid comprising from 2 to 20 carbon atoms.

4. The device of claim 3 wherein said fatty acid is selected from the group consisting of caproic acid, lauric acid, myristic acid, oleic acid, linoleic acid, adipic acid and lanolic acid.

5. A device of claim 1 wherein said fatty acid ester is formed from an alcohol of 2 to 20 carbon atoms.

6. A device of claim 5 wherein said alcohol is an alkanol of 2 to 4 carbon atoms.

7. A device of claim 1 wherein said fatty acid ester is isopropyl myristate.

8. An intravaginal drug delivery device for prolonged release of estrogen and/or progestogen in an amount of 1 to 50% by weight consisting essentially of at least one polyorganosiloxane ring matrix containing an active ingredient to be released, and an amount of 1 to 50% by weight of at least one fatty acid ester.

9. A device of claim 8 wherein the estrogen and/or progestogen is present in an amount of up to 15% by weight.

10. A device of claim 9 wherein said estrogen is 17β-estradiol.

11. A device of claim 1 wherein said active ingredient is selected from the group consisting of progesterone, medroxy-progesterone, norethisterone, trimegestone and norethisterone acetate.

12. A device of claim 1 wherein the active ingredient is a mixture of trimegestone and 17β-estradiol.

13. A device of claim 1 wherein the active ingredient is selected from the group consisting of an antidepressant/ anxiolitic, an Anxiolitic, a Vitamin B6, a Vitamin D, a Vitamin E, an antifungal, an opoid analgesic, a non-opoid analgesic and an antiviral or a compound for its use in the treatment of endometriosis.

14. A device of claim 1 wherein the active ingredient is selected from the group consisting of Fluphenazine, Flupenthixol, Haloperidol, Buspirone, Alprazolam, Trifluoperzine, Piridoxine, Pridoxal, Pyridoxamine, Cholecalciferol, Dihydrotachysterol, Ergocalciferol, Alfacalcidol, d-Alpha-Tocopherol, Clotrimazole, Enconazole, Iltraconazole, Buprenorphine, Levorphanol, Phenoperidine, Fentanyl, Methadone, Mefenamic acid, Acylclovir, Vidarabine, Arildone, Idoxuridine, Gestrinone and Mifepristone.

15. A device of claim 14 wherein the active agent is Mifepristone.

16. A method of treatment of a female warm-blooded animal to combat condition resulting from oestrogen deffi-ciency comprising intravaginally administering into the animal's vagina a device of claim 8.

17. A method of inducing contraception in a female warm-blooded animal comprising injecting into the animal's vagina a device of claim 1 wherein the active ingredient is a contraceptive compound.

18. An intravaginal drug delivery device for prolonged release of an active ingredient consisting essentially of at least one polyorganosiloxane ring matrix containing an active ingredient to be released, and an amount of 1 to 50% by weight of at least one fatty acid ester, wherein the polyorganosiloxane matrix is a central polymer matrix core surrounded by a rate controlling membrane comprising the same polymer as the polymer matrix.

19. An intravaginal drug delivery device for prolonged release of an active ingredient consisting essentially of at least one polyorganosiloxane ring matrix containing an active ingredient to be released daily of up to 500 µg per day sustained up to 12 months in a zero order pattern, and an amount of 1 to 50% by weight of at least one fatty acid ester.

* * * * *